(12) United States Patent
Weinzweig

(10) Patent No.: US 12,016,770 B2
(45) Date of Patent: *Jun. 25, 2024

(54) PROSTHETIC IMPLANT DELIVERY DEVICE AND METHOD

(71) Applicant: Jeffrey Weinzweig, Newport, RI (US)

(72) Inventor: Jeffrey Weinzweig, Newport, RI (US)

(73) Assignee: Novaplast Corporation, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/137,597

(22) Filed: Apr. 21, 2023

(65) Prior Publication Data
US 2023/0255748 A1    Aug. 17, 2023

Related U.S. Application Data

(63) Continuation of application No. 17/245,460, filed on Apr. 30, 2021, now Pat. No. 11,633,273, which is a continuation of application No. 16/144,617, filed on Sep. 27, 2018, now Pat. No. 10,993,796, which is a continuation of application No. 14/982,250, filed on Dec. 29, 2015, now Pat. No. 10,105,213.

(51) Int. Cl.
| | |
|---|---|
| *A61F 2/12* | (2006.01) |
| *A61B 17/34* | (2006.01) |
| *A61B 46/00* | (2016.01) |
| *A61B 46/13* | (2016.01) |
| *A61B 90/00* | (2016.01) |
| *A61F 2/52* | (2006.01) |
| *A61B 17/00* | (2006.01) |

(52) U.S. Cl.
CPC ............ *A61F 2/12* (2013.01); *A61B 17/3468* (2013.01); *A61B 46/00* (2016.02); *A61B 46/13* (2016.02); *A61B 90/08* (2016.02); *A61B 2017/00796* (2013.01); *A61F 2230/0067* (2013.01); *A61F 2250/001* (2013.01)

(58) Field of Classification Search
CPC ........ A61F 2/12; A61F 2/0059; A61F 2/0095; A61F 2/0063; A61F 2/52; A61F 13/551; A61F 2002/523; A61F 2002/30718; A61F 2002/30919; A61F 2220/0033; A61F 2240/002
See application file for complete search history.

(56) References Cited

U.S. PATENT DOCUMENTS

| | | | | |
|---|---|---|---|---|
| 3,138,821 | A * | 6/1964 | Macciocchi | E04F 21/165 |
| | | | | 401/265 |
| 3,552,638 | A * | 1/1971 | Quackenbush | A61B 50/30 |
| | | | | 383/200 |
| 3,627,611 | A * | 12/1971 | Bonk | A61B 50/30 |
| | | | | 156/364 |
| 3,769,971 | A * | 11/1973 | Collins | A61B 46/00 |
| | | | | 128/856 |
| 3,938,658 | A * | 2/1976 | Rohde | A61B 50/30 |
| | | | | 206/439 |

(Continued)

*Primary Examiner* — Seema Mathew

(57) ABSTRACT

A prosthetic implant transfer device is provided that may be used to insert a prosthetic implant through a surgical opening. In some embodiments, the device may comprise a flexible sheet of material that may be formed into an elongated hollow structure. The flexible sheet of material includes a plurality of fasteners that may be selected and engaged to define a desired size distal opening.

10 Claims, 7 Drawing Sheets

(56) References Cited

U.S. PATENT DOCUMENTS

| | | | | |
|---|---|---|---|---|
| 4,035,850 A * | 7/1977 | Cresswall | A61F 2/12 | 606/1 |
| 4,143,428 A * | 3/1979 | Cohen | A61F 2/12 | 604/407 |
| 4,955,906 A * | 9/1990 | Coggins | A61B 90/00 | 623/8 |
| 5,067,821 A * | 11/1991 | Young | A61F 5/44 | 383/44 |
| 5,201,779 A * | 4/1993 | Shiao | A61B 17/3468 | 604/59 |
| 5,571,178 A * | 11/1996 | Ledergerber | A61F 2/12 | 623/8 |
| 5,630,843 A * | 5/1997 | Rosenberg | A61B 90/02 | 604/890.1 |
| 5,813,409 A * | 9/1998 | Leahy | A61B 46/00 | 128/850 |
| 5,916,202 A * | 6/1999 | Haswell | A61B 5/150305 | 128/853 |
| 5,970,979 A * | 10/1999 | Christofel | A61B 46/00 | 128/853 |
| 8,641,758 B1 * | 2/2014 | Anderson | A61F 2/12 | 623/7 |
| 9,925,028 B1 * | 3/2018 | Rosenberg | A61F 2/12 | |
| 10,722,335 B1 * | 7/2020 | Rosenberg | A61F 2/12 | |
| 10,939,985 B2 * | 3/2021 | Winn | A61F 2/0095 | |
| 11,311,369 B2 * | 4/2022 | Hristov | A61B 17/3468 | |
| 11,324,581 B2 * | 5/2022 | Heneveld | A61F 2/0095 | |
| 2003/0153927 A1 * | 8/2003 | DiPoto | A61B 17/3439 | 606/108 |
| 2004/0060566 A1 * | 4/2004 | Musso | A61B 46/00 | 128/849 |
| 2005/0192668 A1 * | 9/2005 | Studin | A61F 2/12 | 623/8 |
| 2007/0270742 A1 * | 11/2007 | Guetty | A61F 5/0036 | 604/103.05 |
| 2007/0276484 A1 * | 11/2007 | Abell | A61F 2/12 | 623/7 |
| 2009/0204107 A1 * | 8/2009 | Keller | A61F 2/12 | 606/1 |
| 2010/0154803 A1 * | 6/2010 | Haworth | A61B 46/00 | 128/856 |
| 2010/0280610 A1 * | 11/2010 | Preissman | A61F 2/12 | 623/8 |
| 2011/0035003 A1 * | 2/2011 | Preissman | A61F 2/12 | 623/7 |
| 2011/0082546 A1 * | 4/2011 | Freund | A61F 2/12 | 623/8 |
| 2012/0185042 A1 * | 7/2012 | Preissman | A61F 2/12 | 623/8 |
| 2015/0028056 A1 * | 1/2015 | Massis | A23G 3/28 | 222/107 |
| 2015/0032208 A1 * | 1/2015 | Preissman | A61F 2/12 | 623/8 |
| 2015/0126812 A1 * | 5/2015 | Anderson | A61F 2/12 | 600/203 |
| 2015/0297339 A1 * | 10/2015 | Placik | C01C 1/04 | 623/8 |
| 2016/0038275 A1 * | 2/2016 | Preissman | A61F 2/12 | 623/8 |
| 2016/0095697 A1 * | 4/2016 | Anderson | A61F 2/12 | 623/8 |
| 2016/0374720 A1 * | 12/2016 | Anderson | A61F 2/0095 | 623/8 |
| 2016/0374797 A1 * | 12/2016 | Nguyen | A61F 2/12 | 623/8 |
| 2017/0181841 A1 * | 6/2017 | Weinzweig | A61B 17/3468 | |
| 2018/0070984 A1 * | 3/2018 | Anderson | A61F 2/12 | |
| 2019/0175331 A1 * | 6/2019 | Horndeski | A61F 2/12 | |
| 2019/0185218 A1 * | 6/2019 | Viancin | A21C 15/005 | |
| 2019/0274819 A1 * | 9/2019 | Graf | A61F 2/12 | |
| 2020/0100885 A1 * | 4/2020 | Harvie | A61F 2/0059 | |
| 2020/0222174 A1 * | 7/2020 | Rosenberg | A61F 2/0059 | |
| 2020/0268497 A1 * | 8/2020 | Rosenberg | A61F 2/0059 | |
| 2020/0360051 A1 * | 11/2020 | Bresnick | A61B 17/3431 | |
| 2021/0205069 A1 * | 7/2021 | Gryskiewicz | A61F 2/12 | |
| 2022/0142764 A1 * | 5/2022 | Barbot | A61F 2/12 | |
| 2022/0160491 A1 * | 5/2022 | Zemmel | A61F 2/12 | |
| 2023/0255663 A1 * | 8/2023 | Higdon | A61B 17/3468 | 606/1 |

\* cited by examiner

PROSTHETIC IMPLANT DELIVERY DEVICE AND METHOD

RELATED APPLICATIONS

This patent application is a continuation of U.S. patent application Ser. No. 14/982,250, filed on Dec. 29, 2015, the disclosures of which are incorporated herein by reference in their entirety.

FIELD OF THE INVENTION

This invention is directed to a delivery apparatus for facilitating the insertion of a prosthesis, such as a breast implant, into a surgical pocket, and method for using the device.

BACKGROUND OF THE INVENTION

This invention relates to the placement of prosthetic implants within a patient's body. Prosthetic implants, such as breast implants, pectoral implants, gluteal implants, and others have been used extensively for many years. Prosthetic implants can take many forms, many of which are comprised of a compressible or deformable material, such as silicone. In order to place such an implant within a body or a cavity of a patient, an incision is made to access the desired site of placement and develop the pocket or space between the tissue planes where the implant will reside.

It is desirable that the incision in the patient for the surgical pocket be as small as possible for a variety of reasons including, reduced trauma to the patient, shorter recovery time, and lessened infection risk. The incision is therefore smaller than the implant itself. In order to insert the implant through the incision, a surgeon will manipulate the implant by hand to deform or compress it and guide it through the incision into the surgical pocket. Such direct handling of the implant has several shortcomings.

The time involved in manipulating the implant to guide it through the relatively small incision is greater than with a large incision. This additional surgical time increases the risks of infection and complications from anesthesia. The amount of time required also impacts the costs of the procedure because of the additional time of the physician and staff. In some instances, implant failures in the form of minor damage to the outer surface of the implant can also be caused by the manipulation.

In order to address these problems, one device that has been developed is a flexible tapered funnel to aid in sliding a breast implant through the incision. U.S. Pat. No. 8,211,173 issued to Keller et al. discloses an apparatus and process for delivering a silicone breast implant into a surgical pocket. U.S. Pat. No. 8,211,173 discloses a tapered sleeve having a wider first end for receiving a breast implant, and a smaller second end for insertion into the surgical pocket. By placing the breast implant in the sleeve, a surgeon squeezes the sleeve to deform the breast implant and force it through the second end and into the surgical cavity. In order to accommodate different size implants, the second end of the sleeve is trimmed to create the desired size hole. Transferring of the implant through the sleeve is aided by lubrication of the implant and/or interior surface of the sleeve itself.

While the flexible funnel has provided some advantages, the present invention addresses certain shortcomings to the funnel. Because adjustment of the opening through which the implant is squeezed is done by way of cutting a portion of the end of the sleeve, an error in sizing may result in having to discard the funnel and trim a new one, which can add to the cost of the procedure. Another problem that has been encountered with the funnel results when the force applied to the outside of the funnel to squeeze the implant sufficiently actually damages the implant. In addition to traumatizing the surgical site, the damaged implant cannot be used, which again increases costs. Another problem that has been experienced results when the force required to transfer the implant through the end of the sleeve causes the sleeve itself to burst at a seam. In some instances, the sleeve may fail due to a tear or inadvertent cut at the end of the sleeve accidentally made when the sleeve is trimmed. Although not common, another issue that may occur stems from the open proximal end that receives the implant. Because of the substantial lubrication that is utilized to allow the implant to be transferred through the distal end, possible mishandling of the funnel may result in the implant sliding out of the proximal open end.

The present invention seeks to address these shortcomings and provide an improved device.

SUMMARY OF THE INVENTION

The present invention is directed to a delivery system for inserting a prosthetic implant through a surgical opening. In some embodiments, the system comprises a flexible sheet of material defining a first side portion and a second side portion. Formed with either the first side portion or the second side portion, or both of the first and the second side portions are a plurality of fasteners. The fasteners are adapted to secure the first side portion with the second side portion to form an elongated hollow form that defines a distal opening. In that there are a plurality of fasteners, a surgeon can select desired fasteners so that a desired size of the distal opening is determined by way of the particular fasteners that are used. For example, fasteners towards the edges of the first and second side portions will, when the first and second side portions are secured with one another, define a relatively large distal opening. By contrast, fasteners spaced from the edge of the first or second side portions will, when the first and second side portions are secured with one another, define a smaller distal opening. In a preferred embodiment, the orientation of the fasteners will, when the first and second edge portions are secured to one another result in a hollow, open-ended frustoconical form. In other embodiments, the orientation of the fasteners will, when the first and second edge portions are secured to one another result in a hollow, open-ended cylindrical form.

In yet other embodiments, the sheet of material may be configured such that when the fasteners are engaged, a hollow elongated form that is enclosed except for one open distal end is assembled. As with the previous embodiments, in this embodiment the size of the opening at the distal end is determined by the particular fasteners that are selected.

In yet another embodiment, material is pre-formed as a hollow elongated form that is enclosed except for the distal end portion. The distal end portion defines a first side portion and a second side portion. Formed with either the first side portion or the second side portion, or both of the first and the second side portions are a plurality of fasteners. The fasteners are adapted to secure the first side portion with the second side portion to define a distal opening. In that there are a plurality of fasteners, a surgeon can select desired fasteners so that a desired size of the distal opening is determined by way of the particular fasteners that are used.

In the various embodiments, the material may take on different forms. In one embodiment, the material is a thin flexible transparent plastic or other polymer material, which may be transparent or semi-transparent. In other embodiments, a mesh material, and preferably a graded mesh material, is utilized. With respect to the graded mesh material, it is preferred that in an assembled form, the distal portion of the material is less expandable than the more proximal portions. In so doing, the surgeon transfers the implant towards the distal end through portions of decreasing expansibility.

It is preferred that a lubricant be utilized to aid in transferring the implant through the distal end. The particular lubricant can be provided separately from the system or may be integral with the system. The lubricant may be liquid lubricant or may be a dry lubricant. The lubricant may be ready-to-use, or may require activation, such as by a wetting agent.

The plurality of fasteners may also take several forms. For example, formed with the first side portion may be a connection channel, while the second side may have formed therewith connection zippers, tabs or hooks adapted to be received within the connection channel and be secured therewith. Alternatively, the first side portion may define tabs and the second side portion may define slots adapted to receive the tabs so as to be secured therein.

Although not part of the claimed invention, it should be understood that the present invention may be used with a variety of prosthetic implants. While silicone gel implants such as breast implants are one type of contemplated implant, other implants may be made of solid deformable silicone, such as pectoral or gluteal implants. In addition to silicone-based implants, prosthetics made of other deformable or compressible materials may be used.

These and other features, aspects, and advantages of the present invention will become better understood with reference to the following description and appended claims.

BRIEF DESCRIPTION OF THE DRAWINGS

A fully enabling disclosure of the present invention, including the best mode thereof to one of ordinary skill in the art, is set forth more particularly in the remainder of the specification, including reference to the accompanying drawings.

DESCRIPTION OF THE PREFERRED EMBODIMENTS

Reference will now be made in detail to preferred embodiments of the invention, one or more examples of which are set forth below. Each example is provided by way of explanation of the invention, not limitation of the invention. It will be apparent to those skilled in the art that various modifications and variations can be made in the present invention without departing from the scope or spirit of the invention. For instance, features illustrated or described as part of one embodiment can be used on another embodiment to yield a still further embodiment. Thus, it is intended that the present invention cover such modifications and variations as come within the scope of the appended claims and their equivalents. Other objects, features, and aspects of the present invention are disclosed in the following detailed description. It is to be understood by one of ordinary skill in the art that the present discussion is a description of exemplary embodiments only and is not intended as limiting the broader aspects of the present invention, which broader aspects are embodied in the exemplary constructions.

Figure 1:
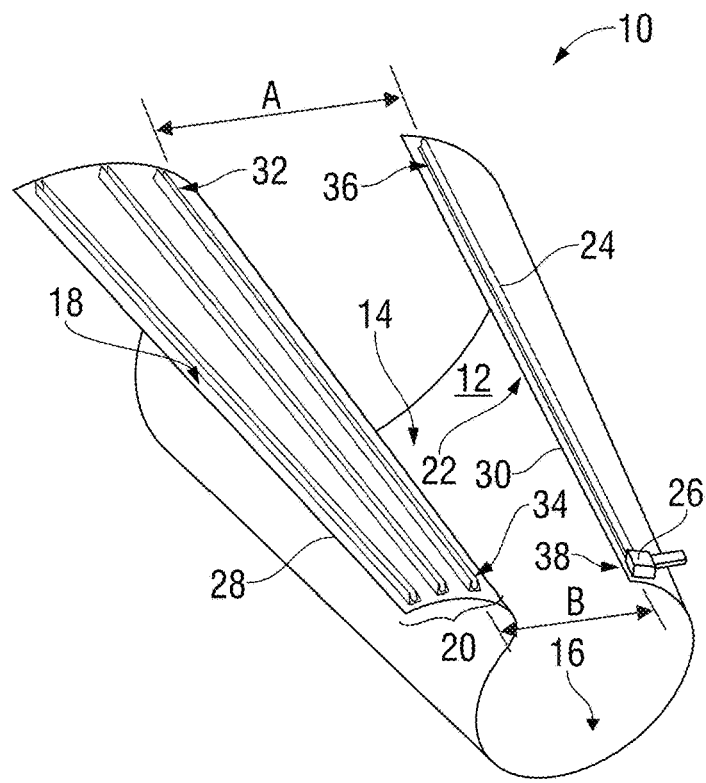
FIG. 1 is a perspective view of a preferred embodiment of the present invention in an unassembled condition.

Referring to FIG. 1, a preferred embodiment of the present invention is depicted in an unassembled form, which is the form in which the device is intended to be provided to users. As shown, prosthetic implant device 10 comprises a sheet of material 12 defining a proximal end 14 and the distal end 16. In this preferred embodiment, formed with a first side portion 18 are a plurality of first fasteners in the form of channels 20, and formed with a second side portion 22 is a second fastener in the form of shoulder 24. The shoulder and channels are configured to be mated to one another in a zip-type manner. Such zip-type fasteners are known in the art, and may comprise a channel in the form of a groove or series of hooks that are adapted to engage the shoulder, which may be generally shaped with arrowhead-like, mushroom shaped cross-section, omega-shaped cross-sectional outline, or the like. Other zip-type engagements may also be utilized. A tab, such as tab 26 may be included. Tab 26 is depicted in schematic form, and is not intended to provide specific details on the zipping operation in that the particular zippers that may be used will be understood by persons of skill in the art. Whether the first fasteners define the groove and the second fastener define the shoulder or vice-versa is a matter of design choice. It should also be understood that the term fastener may denote one part of cooperating structures that act to fasten other structures to one another, such as the groove and shoulder portions of a zip-type fastener.

The flexible sheet further defines a first edge 28 and a second edge 30 that is transverse from the first edge 28. Each of the first fasteners 20 is either integrally formed with the sheet 12 or may be fixed thereto. The first fasteners 20 are disposed in a generally longitudinal relationship with the first edge 28. In this embodiment, each of the first fasteners 20 defines a proximal end 32 and a distal end 34. Similarly, the second fastener defines a proximal end 36 and a distal end 38. The first fasteners 20 are preferably in parallel relationship to one another. The proximal end 32 for each first fastener 20 is positioned a first distance, such as distance A, from the proximal end 36 of the second fastener 24. The distal end 34 of the first fastener 20 is a second distance, such as distance B, from the distal end 38 of the second fastener 24, and the first distance is greater than the second distance.

Figure 2:
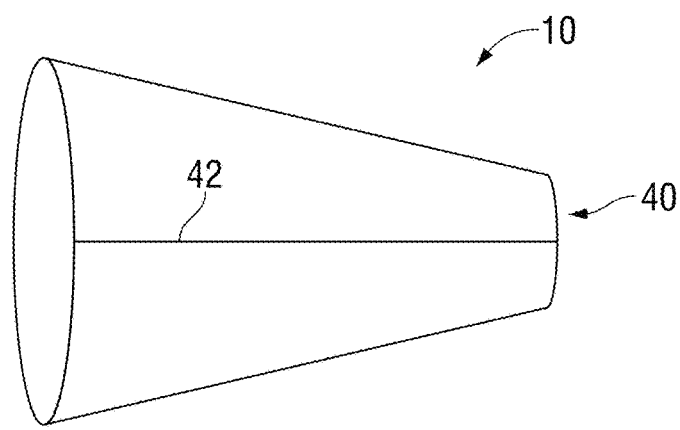
FIG. 2 is a perspective view of the embodiment of FIG. 1 in an assembled condition.

Referring to FIG. 2, prosthetic implant device 10 is depicted in an assembled form. In order to assemble prosthetic implant device 10, a surgeon determines a desired size for a distal opening of the assembled insertion device by evaluating the size of the prosthetic implant that will be transferred through the insertion device. The size of the distal opening of the assembled insertion device can vary based both on the implant size and incision size although more commonly it varies based on the implant size as the incision size for a given procedure, while dependent on surgeon preference, does not vary significantly. The surgeon then selects first fastener from the plurality of first fasteners 20 and engages the second fastener 24 with the selected first fastener. Depending on which first fastener is selected, the resulting distal opening 40 of the formed prosthetic implant device will be larger or smaller. As should be apparent, one of either the plurality of first fasteners 20 or the second fastener 24 should be one an outside surface of the sheet and the other on the inside surface of the sheet. When assembled, the fasteners are not exposed on the interior of the device, and therefore will not contact and potentially damage the implant. As shown, the assembled apparatus includes a seam 42. If desired, a supplemental second fastener can be included. If such a supplemental second fastener is included, it is preferable that the spacing between the first fasteners and the spacing between the second fastener and supplemental second fastener are equal so that the supplemental second fastener may engage one of the first fasteners while the second fastener engages a different first fastener. It should also be appreciated that while the fasteners in the embodiments shown are linear, they may be curved so as to create desired shapes from the sheet of material.

Figure 3:
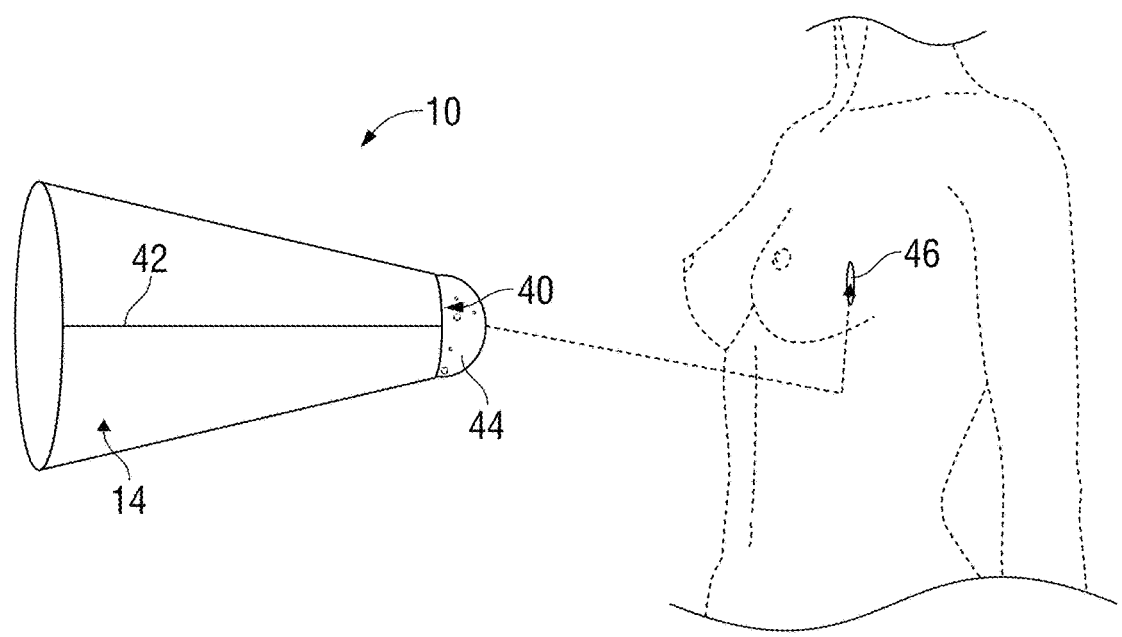
FIG. 3 is a perspective view of the embodiment of FIG. 1 during possible use.

Referring to FIG. 3, a prosthetic implant 44 is placed within the formed prosthetic implant device 10. The surgeon applies a force to the proximal end 14 of the device 10 to transfer the implant 44 distally through the distal opening 40, and through incision 46. The distal end of the device 10 is typically inserted 5-10 mm within the incision 46 as the implant 44 is transferred through the incision 46 into the pocket that had been created by the surgeon to receive it. In this particular example, the incision is made in the inframammary fold beneath the breast, however, the incision may also be made through any incision, such as transaxillary and periareolar. This ensures "touchless" and uninterrupted passage and transfer of the implant 44 through the implant device 10 into the surgical pocket while minimizing risk of inadvertent external delivery of the implant 44 or direct contact of the implant 44 with the skin.

Sheet 10 is made of a thin sheet of flexible material. In some embodiments, the material may be pliable, yet substantially inextensible. It is also preferred that the material be translucent or transparent. Various material that may be suitable include Mylar®, plastics made from Tygon® brand of plastics, vinyls, polyvinyl chloride, and other similar materials. The material must also be able to be sterilized by way of conventional sterilization techniques. There are numerous materials that may be suitable, as will be understood by persons skilled in the art. For example some suitable materials are disclosed in the aforementioned U.S. Pat. No. 8,211,173, and the disclosure of such materials are incorporated herein by reference.

Figure 4:
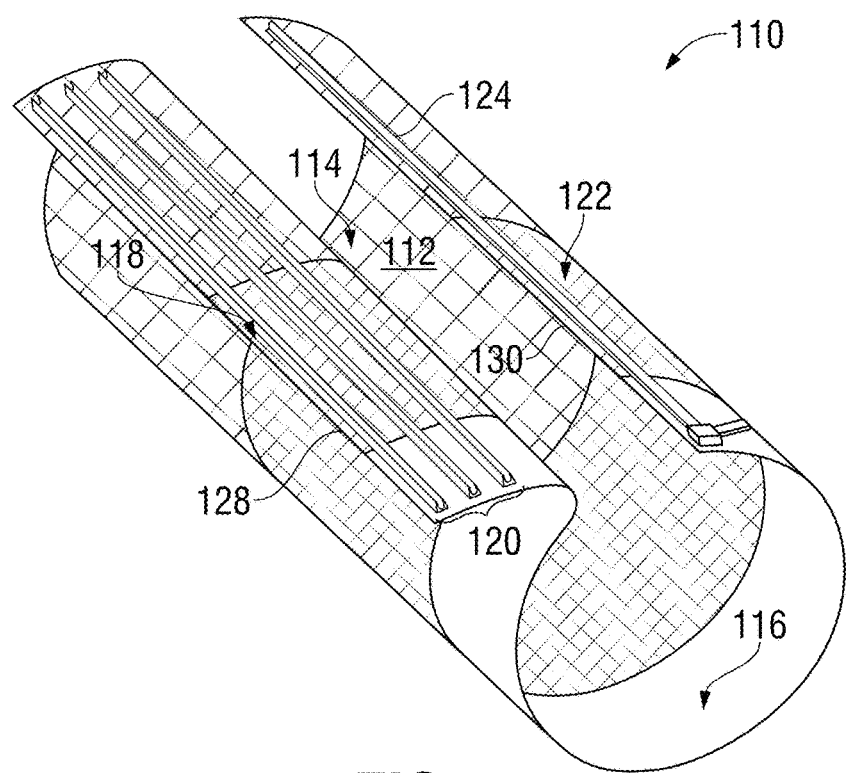
FIG. 4 is a perspective view of an alternative preferred embodiment of the present invention in an unassembled condition.

In other embodiments, the sheet of material may be a mesh. Referring to FIG. 4, a second preferred embodiment of a prosthetic implant device 110 is disclosed. In this embodiment, the sheet of material 112 is formed of a graded mesh. The sheet 112 defines a proximal end 114 a distal end 116. In this embodiment, formed with a first side portion 118 are a plurality of first fasteners in the form of channels 120, and formed with a second side portion 122 is a second fastener in the form of shoulder 124, similar to the previous embodiment.

The flexible sheet 110 further defines a first edge 128 and a second edge 130 that is transverse from the first edge 128. The first fasteners 120 are disposed in a generally longitudinal relationship with the first edge 28. In this embodiment, each of the first fasteners 20 is aligned generally parallel to the first edge. Similarly, the second fastener 124 is aligned generally parallel to the second edge 130.

Figure 5:
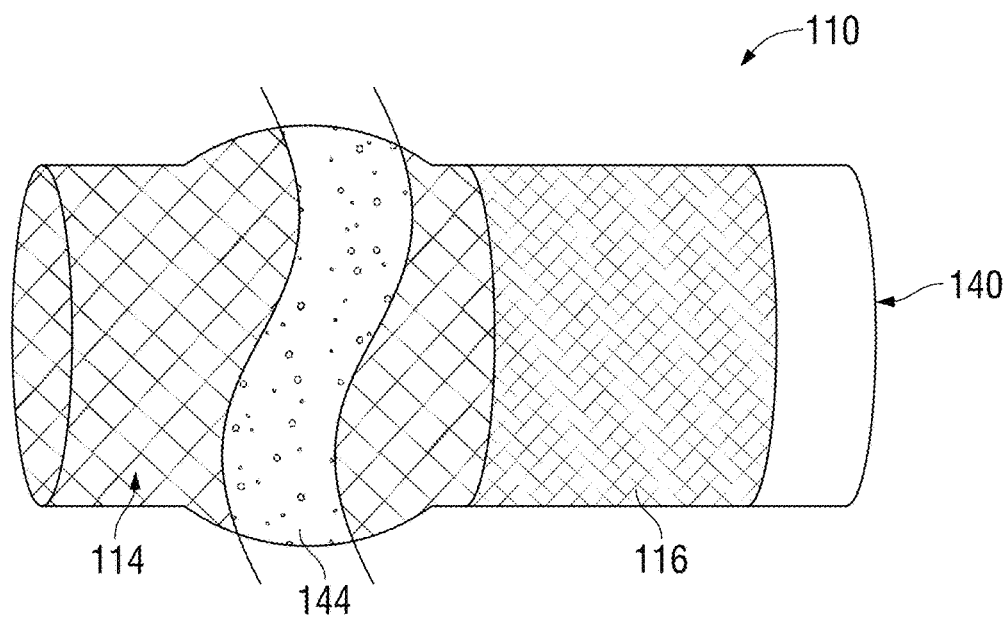
FIG. 5 is a perspective view of the embodiment of FIG. 4 in an assembled condition.

In a preferred form, the sheet of material 112 is a graded mesh that provides greater expandability towards the proximal end 114, and become less expandable towards the distal end 116. The distal end 116 is configured such that it provide sufficient resistance to expansion such that it will cause the implant to deform or compress as it transferred through the distal end. Because the proximal end 114 of the material 112 is expandable, the assembled device need not go from a larger proximal opening to a smaller distal opening. Rather, the device 110 may be cylindrical when assembled as shown in FIG. 5. As depicted, the implant 144 is located within an expanded portion of the proximal end 114 of the device 110. The implant can be inserted through the proximal end, or may be laid on the sheet of material and then the fasteners engaged.

Figure 6:
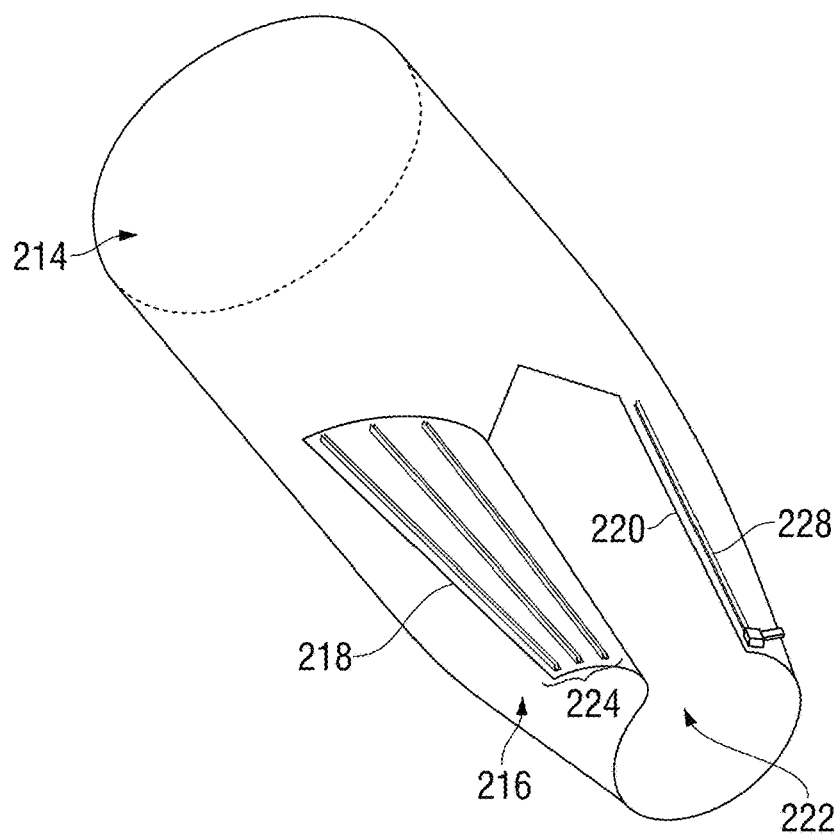
FIG. 6 is a perspective view of another alternative preferred embodiment of the present invention in an unassembled condition.

By providing means for adjusting the size of the distal opening by way of fasteners, in some embodiments, one may insert the implant into the device through the distal end. Referring to FIG. 6, an embodiment that allows for the implant to be placed into the device by way of a distal opening is described. Prosthetic implant device 210 comprises a flexible elongated member 211 defining a proximal end portion 214 that is shown as a cylindrical form. The distal end portion 216 defines a first longitudinal edge 218 and a second longitudinal edge 220. These first and second longitudinal edges define a longitudinal opening 222. A plurality of first fasteners 224 are formed longitudinally adjacent the longitudinal edge 218 on a first portion 226. A second fastener 228 is formed longitudinally adjacent the second longitudinal edge 220 on a second portion 230. Since in this embodiment the first fasteners are located on an exterior portion, the second fastener 228 is formed on an interior portion, and are therefore depicted in phantom. As with the previously described embodiments, the second fastener 228 is selectably engageable with any of the first fasteners 224. The first and second fasteners 224 and 228 are aligned such that when engaged with one another, the longitudinal opening is closed and the distal end portion 216 is of a generally frustoconical shape and defines a distal opening through which the prosthetic implant is transferred.

Figure 6B:
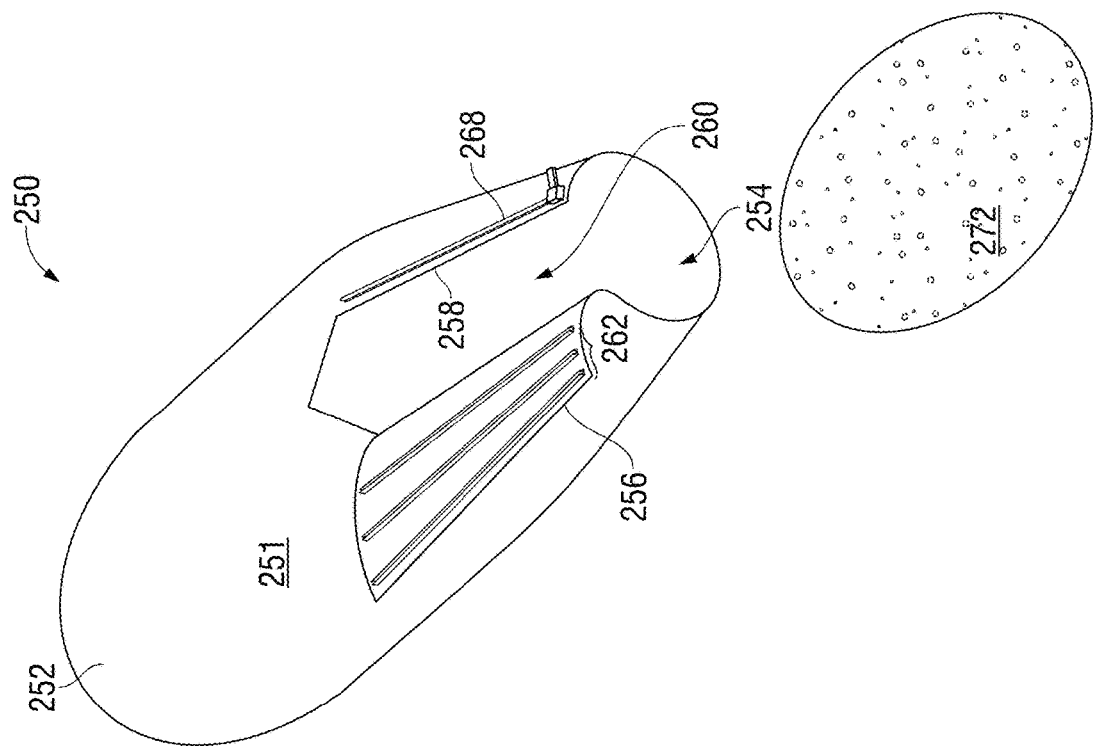
FIG. 6B is a perspective view of the embodiment of FIG. 6A, with an implant.
Figure 6A:
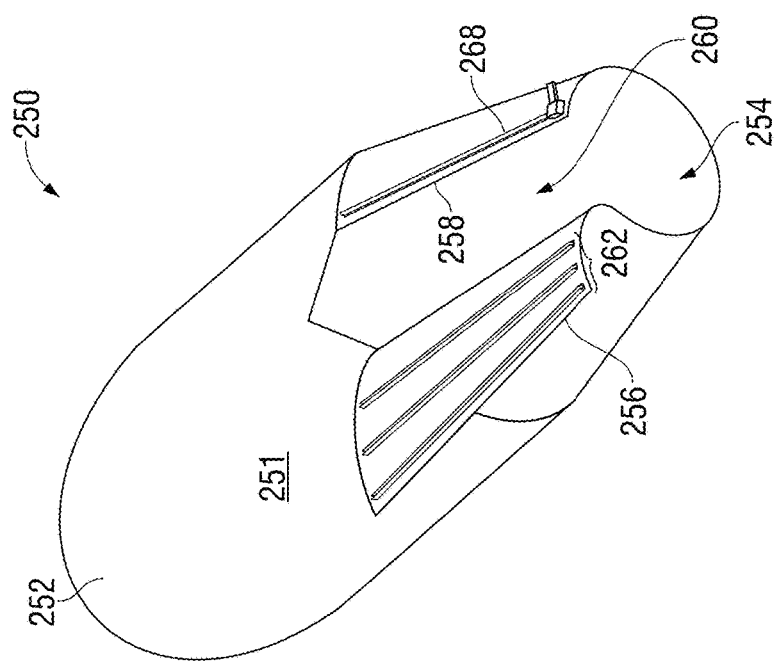
FIG. 6A is a perspective view of another alternative preferred embodiment of the present invention in an unassembled condition.
Figure 6D:
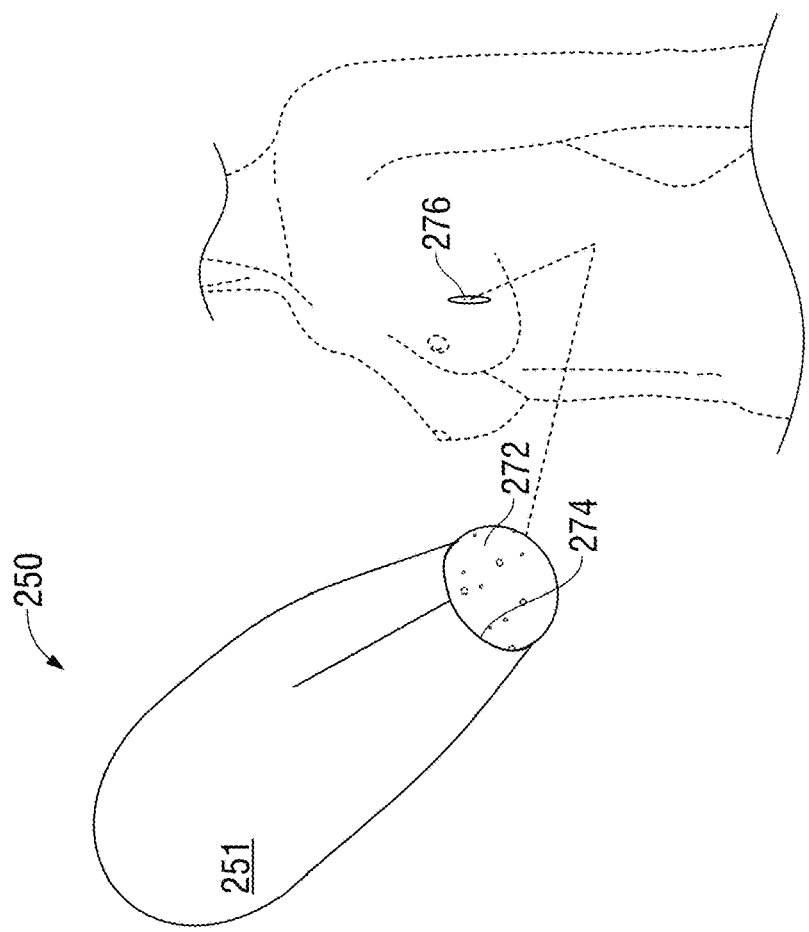
FIG. 6D is a perspective view of the preferred embodiment as shown in FIG. 6A and FIG. 6B in use.
Figure 6C:
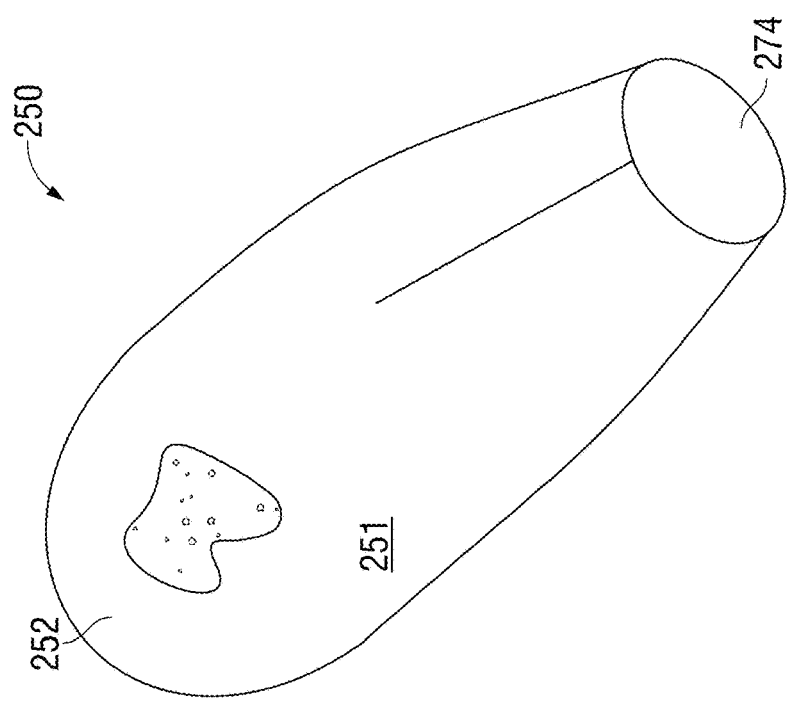
FIG. 6C is a perspective view of the preferred embodiment as shown in FIG. 6A and FIG. 6B in an assembled condition.

Referring to FIG. 6A, a variation on the embodiment of FIG. 6 is shown. In this variant, prosthetic implant device 250 comprises a flexible elongated member 251 defining a proximal end portion 252 that is shown as a closed end. As with the embodiment shown in FIG. 6, the distal end portion 254 defines a first longitudinal edge 256 and a second longitudinal edge 258. These first and second longitudinal edges define a longitudinal opening 260. A plurality of first fasteners 262 are formed longitudinally adjacent the longitudinal edge 264. A second fastener 268 is formed longitudinally adjacent the second longitudinal edge 270. In this variant, an implant would be placed within the elongated member prior to forming the distal end opening. Referring to FIGS. 6B-D, implant 272 is inserted into elongated member 251. The longitudinal opening 260 is closed by fastening second fastener 268 with one of the plurality of first fasteners 262, and a distal opening 274 is defined. The elongated member is then positioned such that the implant 272 is allowed to slide towards the distal opening 274. The physician then transfers the implant through the distal opening and through the incision 276.

Figure 7:
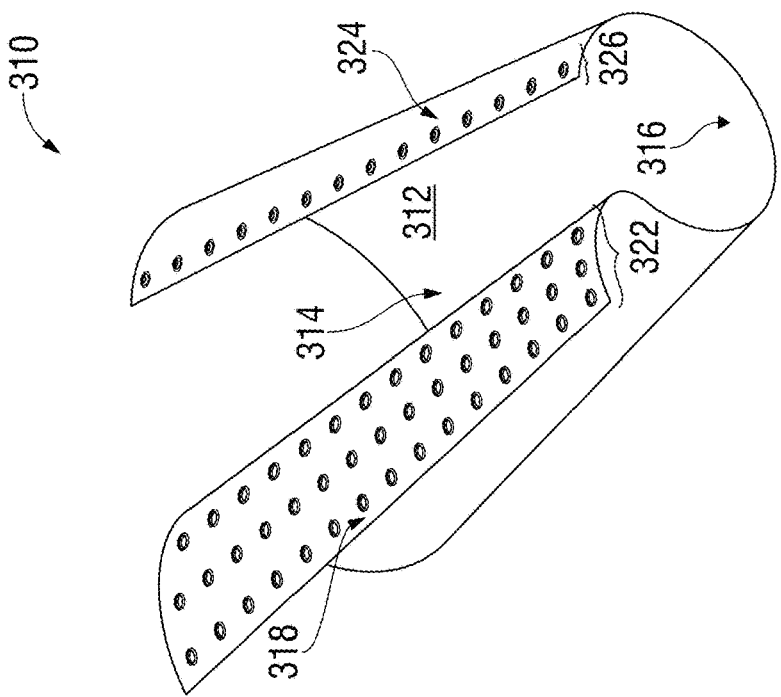
FIG. 7 is a perspective view of another alternative preferred embodiment of the present invention in an unassembled condition.

The plurality of fasteners depicted in the above embodiments have been zip-type fasteners. It should be understood, however, that the fasteners may take other forms. For example, referring to FIG. 7 an embodiment similar to that depicted in FIG. 1 is shown. In FIG. 7, the prosthetic implant device 310 comprises a sheet of material 312 defining a proximal end 314 and the distal end 316. In this preferred embodiment, formed with a first side portion 318 are a plurality of first fasteners in the form of a series of snap attaching units 322, and formed with a second side portion 324 is a second fastener in the form of a series of snap closure units 326. The attaching units and closure units are configured to be mated to one another. Other snap-type engagements may also be utilized. Whether the first fasteners define the attaching units and the second fastener define the closure units or vice-versa is a matter of design choice. Again, the reference to a first fastener or a second fastener denotes one part of cooperating structures that act to fasten other structures to one another.

Figure 8:
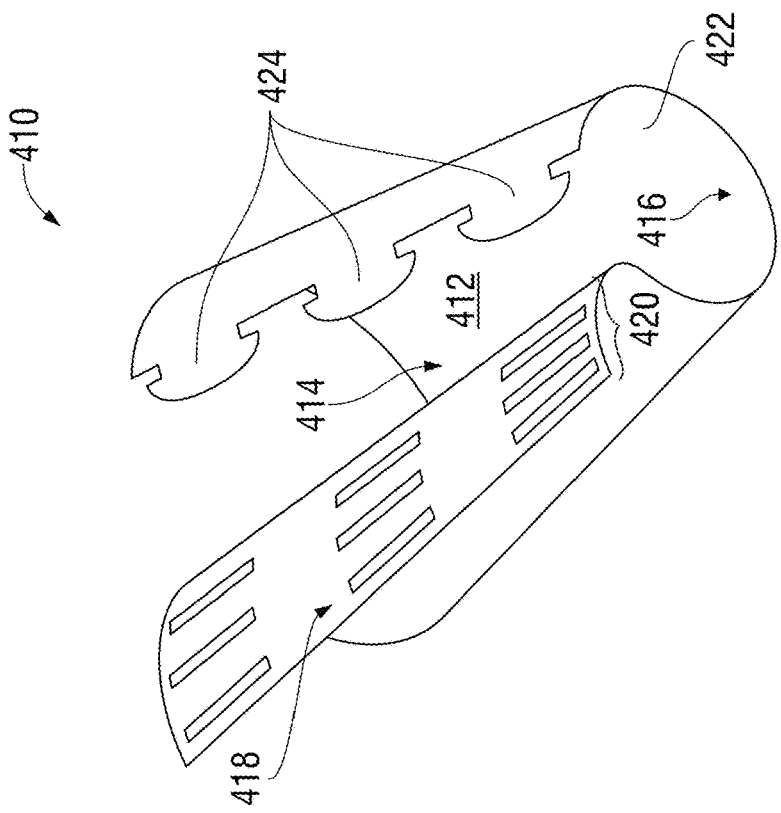
FIG. 8 is a perspective view of another alternative preferred embodiment of the present invention in an unassembled condition.

Referring to FIG. 8 is another preferred fastener arrangement. In this embodiment, the prosthetic implant device 410 comprises a sheet of material 412 defining a proximal end 414 and the distal end 416. Formed with a first side portion 418 are a plurality of first fasteners in the form of a series of receiving slots 420, and formed with a second side portion 422 is a second fastener in the form of a series of tabs 424. The slots and tabs are configured to be mated to one another. Other slot and tab type engagements may also be utilized.

Figure 9:
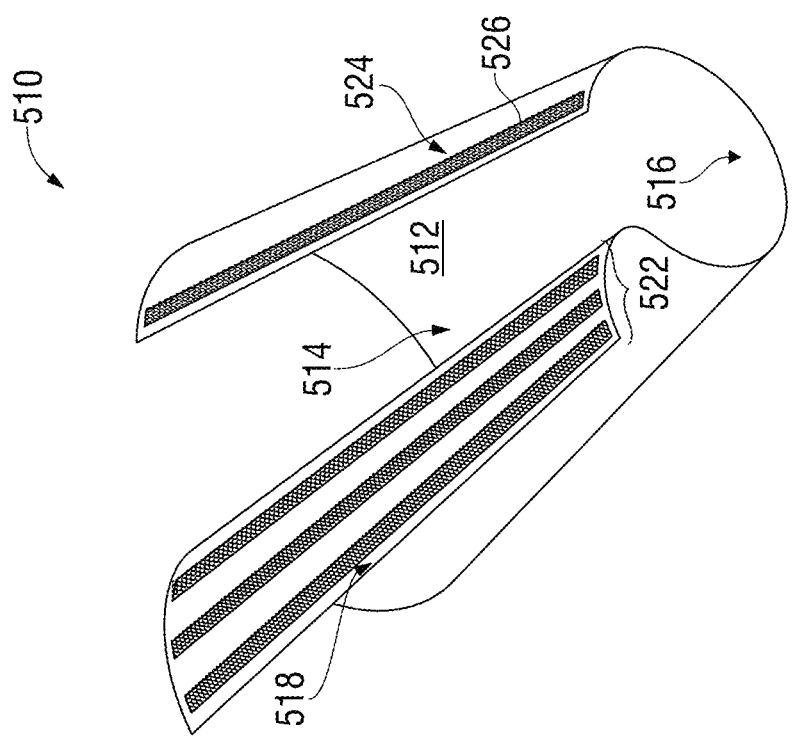
FIG. 9 is a perspective view of another alternative preferred embodiment of the present invention in an unassembled condition.

Other contemplated fasteners include a hook and loop enclosure arrangement. Such an embodiment is shown in FIG. 9. Here, the prosthetic implant device 510 comprises a sheet of material 512 defining a proximal end 514 and the distal end 516. In this preferred embodiment, formed with a first side portion 518 are a plurality of first fasteners in the form of a series of either the hook or loop portion of a hook and loop enclosure 522. Formed with a second side portion 524 is a second fastener in the form of the opposing portion of the hook and loop enclosure 526. The hook and loop portions are configured to be mated to one another. Whether the first fasteners define the hook portion and the second fastener define the loop portion or vice-versa is a matter of design choice.

Figure 10:
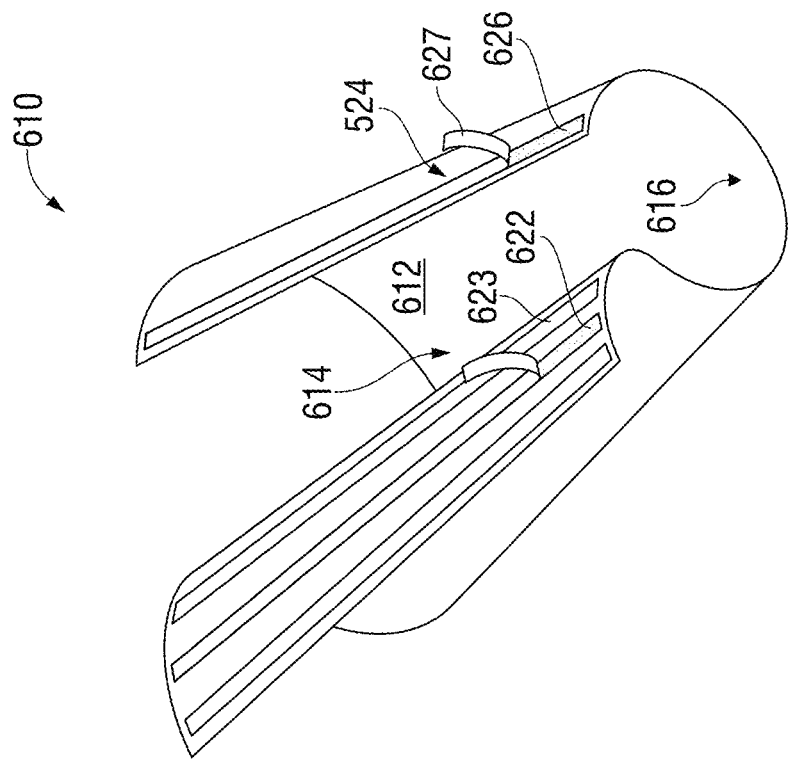
FIG. 10 is a perspective view of another alternative preferred embodiment of the present invention in an unassembled condition.

While in the above examples, cooperating structures are used to fasten the first side portion and the second side portion of a sheet, other fasteners such as an adhesive may be utilized. The adhesive may be a pressure adhesive, or may be an adhesive strip that is exposed by removing a covering strip. One such embodiment is shown in FIG. 10. Here, the prosthetic implant device 610 comprises a sheet of material 612 defining a proximal end 614 and the distal end 616. In this preferred embodiment, formed with a first side portion 618 are a plurality of first fasteners in the form of adhesive strips 622 on designated portions of the surface of the sheet 612. Formed with a second side portion 324 is a second fastener in the form of an adhesive strip 626. The adhesive strips 622 and 626, prior to assembly, may include release strips 623 and 627. It should also be noted, that as an alternative to the embodiment in FIG. 10, that only one adhesive strip may be required. In such a case, for example, adhesive strips 622 would not be included, and instead, indicators would be marked on the surface of the sheet 612 to designate where adhesive strip 626 should be attached for use. It should further be noted that whether the first fasteners comprise the adhesive and the second fastener define the sheet surface is a matter of design choice.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention which is set forth in the following claims. In addition, it should be understood that aspects of the various embodiments may be interchanged, both in whole, or in part. Therefore, the spirit and scope of the appended claims should not be limited to the description of the preferred versions contained therein.

I claim:

1. A device adaptable to facilitate insertion of a prosthetic through a surgical opening of a patient, the device comprising:
    an elongated flexible elastomeric member defining a proximal end portion, a distal end portion, an interior and an exterior;
    the interior adapted to receive therein the prosthetic; and
    the distal end portion including cooperating detachable mechanical fasteners adapted to secure to one another and form a distal opening in the distal end portion.

2. The device of claim 1, wherein the proximal end portion is closed.

3. The device of claim 1, wherein securement of the mechanical fasteners is selectable to adjust a size of the distal opening.

4. The device of claim 1, wherein at least a first mechanical fastener is with the interior and at least a second mechanical fastener is with the exterior.

5. The device of claim 1, further comprising a first longitudinal edge portion extending from the distal end portion and a second longitudinal edge portion extending from the distal end portion, the mechanical fasteners comprises a first fastener along the first longitudinal edge portion and a second fastener along the second longitudinal edge portion.

6. The device of claim 5, wherein the proximal end portion is closed.

7. The device of claim 5, wherein securement of the mechanical fasteners is selectable to adjust a size of the distal opening.

8. The device of claim 5, wherein at least a first mechanical fastener is with the interior and at least a second mechanical fastener is with the exterior.

9. A device configurable to facilitate insertion of a prosthetic implant through a surgical opening of a patient, the device comprising:
    a flexible sheet having a first lateral portion and a second lateral portion, the first lateral portion being engageable with the second lateral portion; and when configured to facilitate insertion of the prosthetic implant, the first lateral portion is engaged with the second lateral portion, and the device further comprises a closed proximal end and an open distal end, wherein the distal end is of a size to urge the prosthetic implant through the surgical opening.

10. A device adaptable to facilitate insertion of a prosthetic through a surgical opening of a patient, the device comprising:

an elongated flexible elastomeric member defining a proximal end portion, a distal end portion, an interior and an exterior;

the interior adapted to receive therein the prosthetic; and the distal end portion including cooperating detachable mechanical fasteners adapted to secure to one another and form a distal opening in the distal end portion, wherein securement of the mechanical fasteners is selectable to adjust a size of the distal opening, and, wherein the proximal end portion is closed.

* * * * *